United States Patent [19]

Ferrari et al.

[11] 4,199,579
[45] Apr. 22, 1980

[54] CARBAMATES OF 2-HALOERGOLINES AND 2-HALOERGOLENES AND PROCESS FOR THE PREPARATION THEREOF

[75] Inventors: Giorgio Ferrari; Vittorio Vecchietti, both of Milan, Italy

[73] Assignee: Siphar S. A., Lugano, Switzerland

[21] Appl. No.: 873,541

[22] Filed: Jan. 30, 1978

Related U.S. Application Data

[63] Continuation-in-part of Ser. No. 666,171, Mar. 12, 1976, abandoned.

[30] Foreign Application Priority Data

Mar. 14, 1975 [CH] Switzerland ............................ 3273/75

[51] Int. Cl.$^2$ .................... C07D 457/02; A61K 31/48
[52] U.S. Cl. ............................... 424/248.55; 424/250; 424/261; 544/125; 544/361; 546/67
[58] Field of Search ...................... 260/285.5, 268 PE; 424/261, 250, 248.55; 544/125, 361; 546/67

[56] References Cited

U.S. PATENT DOCUMENTS

| | | | |
|---|---|---|---|
| 2,516,002 | 7/1950 | Hofmann et al. | 260/285.5 |
| 3,228,943 | 1/1966 | Bernardi et al. | 544/361 |
| 3,236,852 | 2/1966 | Bernardi et al. | 260/285.5 |
| 3,704,233 | 11/1972 | Eich et al. | 260/285.5 |
| 3,752,814 | 8/1973 | Fluckegar et al. | 260/268 PE |
| 3,904,634 | 9/1975 | Arcari et al. | 260/285.5 |
| 3,920,664 | 11/1975 | Clemens et al. | 260/268 PE |
| 3,944,582 | 3/1976 | Ferrari et al. | 260/285.5 |
| 3,959,288 | 5/1976 | Bach et al. | 260/285.5 |
| 4,057,635 | 11/1977 | Ferrari et al. | 544/361 |

FOREIGN PATENT DOCUMENTS 625559  8/1948  United Kingdom .................. 260/285.5

OTHER PUBLICATIONS

Troxler et al., Helv. Chim. Acta vol. 40, pp. 2160–2170 (1957).

*Primary Examiner*—Mary C. Lee
*Attorney, Agent, or Firm*—Cushman, Darby & Cushman

[57] ABSTRACT

A number of pharmacologically active ergoline derivatives are disclosed, their preparation is described and examples of suitable pharmaceutical preparations are presented. Of quite particular interest among the rich series of compounds afforded by the present invention are D-2-bromo-1,6-dimethyl-8beta-(perhydroazepinylcarbonyloxymethyl)-ergoline and its salts (especially maleate and methanesulfonate) for the treatment of psychogenetic disorders, and D-2-bromo-6-methyl-8beta-(morpholinocarbonyloxymethyl)-ergoline and its salts (especially the maleate and the methanesulfonate for the treatment of asthma and allied ailments. Good tolerability, low toxicity and high effectiveness distinguish these compounds over those of the prior art.

25 Claims, No Drawings

CARBAMATES OF 2-HALOERGOLINES AND 2-HALOERGOLENES AND PROCESS FOR THE PREPARATION THEREOF

This is a continuation-in-part application of our U.S. Ser. No. 666,171 filed on Mar. 12, 1976, now abandoned.

The present invention relates to the preparation and the use of compounds having the following general formula:

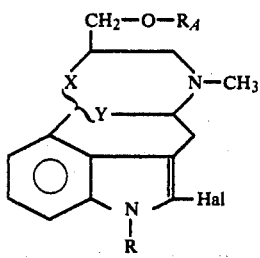

wherein the radicals R, $R_A$, x⌒y, Hal have the following meanings:

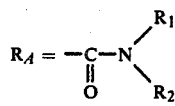
(a)

in which $R_1$ and $R_2$ in turn represent H; $C_1$-$C_8$ alkyls, straight or branched; ($C_3$-$C_{12}$) alicyclic radicals; phenyl, benzyl, phenethyl, substituted in the aromatic ring and/or in the aliphatic chain with one or more groups selected among alkyls, alkoxyls, a dioxymethylene group, hydroxyl, halogens; $R_1$ and $R_2$ possibly being moreover combined to each other as

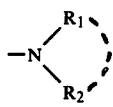

to form one or more rings containing ($C_2$-$C_{12}$) members (e.g. to form a piperidino, hexamethylenimino, azabicyclo [3, 2, 2] nonane radical etc.) or connected by chains containing also heteroatoms such as for example

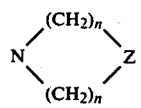

wherein Z represents an oxygen atom, N-$R_3$ (in which $R_3$ is H, alkyl, phenyl aralkyl, etc. and n=2-4), to form heterocyclic group such as morpholine, piperazine;
(b) R=H, $C_1$-$C_5$ alkyl, straight or branched;
(c) x⌒y can be the radical —$CH_2$—CH< (in both the possible stereoisomeric configurations) or the radical —CH=C<; and
(d) Hal=Cl, Br, I.

It has been found that the compounds having the general formula (I) can be prepared starting from compounds having the following general formula:

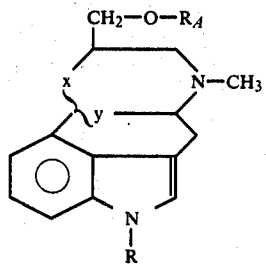

wherein R, $R_A$, x⌒y have the above described meaning, through the halogenation by means of a N-halo-acylamide, particularly among N-bromo-acetamide, N-bromosuccinimide, N-chlorosuccinimide, N-iodosuccinimide, or by means of derivatives of the type chlorobenzotriazole, in aprotic solvents, such as dioxane, tetrahydrofuran, ethyleneglycol dimethylether, diethyleneglycol, dimethylether, etc. at a temperature of between −10° C. and +150° C.

The resulting halogenated compounds are isolated and purified according to the commonly known chemical methods, for instance by crystallization or by chromatography on a column packed with $SiO_2$, $Al_2O_3$, Florisil, etc. The novel compounds obtained according to the present invention are generally solid and crystalline at room temperature and form solid and almost always crystalline salts with acids.

The acids used for the preparation of these salts can be for example inorganic (hydrochloric, hydrobromic, sulphuric acid) or organic (e.g. maleic, tartaric, methansulphonic acid).

In the following examples some general methods for the preparation of the novel compounds of the invention having general formula (I) are described. Furthermore there are listed the novel compounds prepared according to the present invention together with their chemical and physical properties.

The examples are intended only as illustrating and not limiting the invention.

EXAMPLE 1

A solution of D-6-methyl-8beta-(N,N-dimethyl-carbamoyloxymethyl)-9, 10-didehydroergoline (1.0 g) in anhydrous dioxane (60 mls) is supplemented, under stirring and under nitrogen, at room temperature with a solution of N-bromosuccinimide (0.7 g) in anhydrous dioxane (20 mls.). The reaction mixture is heated to 65° C. for 15 minutes, then cooled to room temperature and poured in a 2 N water solution for $Na_2CO_3$ (120 mls). The resulting solution is extracted three times with chloroform, the combined extracts are washed with water and dry evaporated at temperatures lower than 40°-45° C. The residue is chromatographed over a deactivated silica gel column (100 g) and the pure product, as indicated by the roman number I in the following list of the compounds prepared according to the invention, is eluted with $CH_2Cl_2+1\%$ $CH_3OH$ and crystallized from ethyl ether.

EXAMPLE 2

To a solution of D-6-methyl-8beta-(perhydroazepinylcarbonyloxymethyl)-ergoline (2 g) in anhydrous dioxane (120 mls) there is added, under stirring and under nitrogen, a solution of N-bromosuccinimide (1.12 g) in anhydrous dioxane (50 mls). The reaction mixture is heated to 75° C. and maintained at this temperature during 3 hours. It is then poured over a ice-water mixture, alkalinized with NH4OH and extracted with chloroform. The extracts are washed with water, dried over Na2SO4 and dry evaporated. The product (II) is obtained in pure form after chromatography on silica gel (150 g) by elution with CH2Cl2+1% MeOH.

EXAMPLE 3

To a solution of D-6-methyl-8beta-(perhydroazepinylcarbonyloxymethyl)-ergoline (2 g) in anhydrous tetrahydrofurane (50 mls) there is added at room temperature a solution of N-chlorobenzotriazole in tetrahydrofurane (20 mls). After 15 minutes the reaction mixture is poured in water, alkalinized with NH4OH and extracted with ether. The extracts are washed with a saturated NaCl solution and dry evaporated. The product (III) is obtained in pure form after chromatography on SiO2 by eluting with CH2Cl2+0.5% MeOH.

According to the same method other compounds have been prepared, which are contemplated in the scope of the formula (I), as synthetically indicated in the following Table 1, in which:

In the first column the starting compound is shown, together with the related meanings of the radicals R, $R_A$ and of the group x⌢y.

In the second column the reagent is shown, by the following abbreviations:
NBS = N-bromosuccinimide
NBA = N-bromoacetamide
NIS = N-iodosuccinimide In the third column the reaction conditions are reported, and more particularly:
(a) the solvent, by means of the following abbreviations:
GED = ethyleneglycol dimethylether
DX = dioxane
THF = tetrahydrofurane
GDD = Diethyleneglycol dimethylether
(b) the reaction temperature (°C.)
(c) the reaction time (minutes)

In the fourth column the reaction product is indicated, it being identified through the meanings of R, $R_A$ and of the x⌢y group.

Later on the chemical and physical characteristics and properties of the thus prepared product are listed, the Roman number corresponding to that of the corresponding Examples.

TABLE I

| | Starting compound | | | | Reaction product | | | |
|---|---|---|---|---|---|---|---|---|
| Ex. | R | $R_A$ | x⌢y | reactant | Solvent, temperature (°C.) Reaction time (minutes) | R | $R_A$ | x⌢y | Hal |
| 4 | H | CON(CH3)(CH3) | CH2—C(CH3)/ | NBS | DX,50 15' | H | CO—N(CH3)(CH3) | CH2—CH/ | Br |
| 5 | H | CON(E)(Et) | CH=C/ | NBS | DX,-5 120 | H | CON(E)(Et) | CH=C/ | Br |
| 6 | H | CON(E)(Et) | CH2—CH/ | NBS | DX,50 30' | H | CON(Et)(Et) | CH2—CH/ | Br |
| 7 | H | CO—N⬠ | CH2—CH/ | NBS | DX,50 60' | H | CON⬠ | CH2—CH/ | Br |
| 8 | CH3 | CO—N⬠ | CH2—CH/ | NBA | THF,-5 15' | CH3 | CON⬠ | CH2—CH/ | Br |
| 9 | H | CO—N⬠ | CH=C/ | NBS | THF,0 60' | CH3 | CON⬠ | CH=C/ | Br |
| 10 | H | CO—N⬠ | CH2—CH/ | NBS | DX,50 120' | H | CON⬠ | CH2—CH/ | Br |

TABLE I-continued

| Ex. | Starting compound R | R_A | x⌢y | reactant | Solvent, temperature (°C.) Reaction time (minutes) | Reaction product R | R_A | x⌢y | Hal |
|---|---|---|---|---|---|---|---|---|---|
| 11 | H | CO—N(piperidinyl) | CH=C< | NBS | DX, 25  60' | H | CON(piperidinyl) | CH=C< | Br |
| 12 | H | CO—N(piperidinyl) | CH₂—CH< | NBS | DX, 50  120' | H | CON(piperidinyl) | CH₂—CH< | Br |
| 13 | H | CON(perhydroazepinyl) | CH=C< | NBS | DX, 25  30' | H | CON(perhydroazepinyl) | CH=C< | Br |
| 14 | CH₃ | CON(perhydroazepinyl) | CH=CH< | NBA | THF, -5  30' | CH₃ | CON(perhydroazepinyl) | CH₂—CH< | Br |
| 15 | H | CON(perhydroazepinyl) | CH₂—CH< | NIS | DX, 25  60' | H | CON(perhydroazepinyl) | CH₂—CH< | I |
| 16 | H | CON(morpholinyl) | CH₂—CH< | NBS | GED, 25  30' | H | CON(morpholinyl) | CH₂—CH< | I |
| 17 | CH₃ | CON(morpholinyl) | CH₂—CH< | NBS | GED, 60  120' | CH₃ | CON(morpholinyl) | CH₂—CH< | Br |
| 18 | H | CON(piperazinyl)NCH | CH₂—CH< | NBA | GED, 60  120' | H | CON(piperazinyl)NCH₃ | CH₂—CH< | Br |
| 19 | H | CON(bicyclic) | CH=CH< | NBS | DX, 25  60' | H | CON(bicyclic) | CH=C< | Br |
| 20 | H | CON(bicyclic) | CH₂—CH< | NBS | DX, 60  120' | H | CON(bicyclic) | CH₂—CH< | Bn |
| 21 | H | CONH—CH(CH₃)—CH₂—φ | CH=C< | NBS | DX, 25  60' | H | CONH—CH(CH₃)—CH₂—φ | CH=C< | Br |

(I) D-2-bromo-6-methyl-8beta-(N,N-dimethylcarbamoyloxymethyl)-9,10-didehydroergoline m.p. 187°-9° C. (ethyl ether); $[\alpha]_D^{20}+46.3°$ (c=0.5, C₅H₅N); M+ (m/e) 403,405.

For C₁₉H₂₂N₃O₂Br (404.3): calc. %C, 56.44; H, 5.48; N, 10.39; found %C, 56.88; H, 5.71; N, 9.97; u.v. (MeOh) $\lambda_{max}$302 nm (ε 11700), 242 nm (ε 23000), 228 nm (ε 21500), I.R. (KBr) 1675, 1603 cm⁻¹.

(II) D-2-bromo-6-methyl-8beta-(perhydroazepinylcarbonyloxymethyl)-ergoline, m.p. 182°-4° C. (ethyl ether); $[\alpha]_D^{20}-87.0°$ (c=9,5, C₅H₅N); M+ (m/e) 459, 461.

For C₂₃H₃₀N₃O₂Br (460.4): calc. %C, 60.0; H, 6.57; N, 9.13; found %C, 60.47; H, 6.65; N, 9.15; u.v. (MeOH) 280 nm (ε 9220) 22 nm (ε 32460), I.R. (KBr) 1725, 1680, 1603 cm⁻¹.

(III) D-2-chloro-6-methyl-8beta-(perhydroazepinylcarbonyloxymethyl)-ergoline, m.p. 179°-181° C. (ethyl acetate), m.p. 215°-18° C. (tartrate); $[\alpha]_D^{20}=-70.5$ (c=0.5 C₅H₅N) (tartrate); M+ 417, 415.

For $C_{23}H_{30}N_3O_2Cl$ (415.9): calc. %C, 66.41; H, 7.27; N, 10.10; found %C, 66.50; H, 7.07; N, 9.49; u.v. (MeOH) $\lambda_{max}$273 ($\epsilon$ 9380), 225 ($\epsilon$ 33200), I.R. (KBr) 1690 cm$^{-1}$.

(IV) D-2-bromo-6-methyl-8beta-(N,N-dimethylcarbamoyloxymethyl)-ergoline m.p. 232°–234° C. (EtOAc); $[\alpha]_D^{20} = -78$ (0.5% in MeOH); M+ 405–407.

For $C_{29}H_{24}N_3O_2Br$ (406.33): calc. %C, 56.16; H, 5.95; N, 10.34 found %C 56.22; H, 6.13; N, 9.96; u.v. (MeOH) $\lambda_{max}$282 ($\epsilon$ 9700), 226 ($\epsilon$ 34400), I.R. (KBr) 1675, 1607 cm$^{-1}$.

(V) D-2-bromo-6-methyl-8beta-(N,N-diethylcarbamoyloxymethyl-9,10-didehydroergoline maleate, m.p. 185°–187° C.; (EtOH); $[\alpha]_D^{20} + 42$ (c=0.5 $C_5H_5N$); M+ 433-431.

For $C_{25}H_{30}N_3O_6Br$ (548.49): calc. %C, 54.75; H, 5.51; N, 7.66; found %C, 54.77; H, 5.44; N, 7.39; u.v. (MeOH) $\lambda_{max}$303 (10.400), 213 (32.000), I.R. (KBr) 1685.

(VI) D-2-bromo-6-methyl-8beta-(N,N-diethylcarbamoyloxymethyl)-ergoline, m.p. 159°–161° C. (EtOAc); $[\alpha]_D^{20} - 68$ (c=0.5 MeOH); M+ 435-433.

For $C_{21}H_{28}N_3O_2Br$ (434.4): calc. %C, 58.06; H, 6.50; N, 9.67; found %C, 58.01; H, 6.38; N, 9.24; u.v. (MeOH) $\lambda_{max}$277 (9160), 227 (30.900), I.R. (KBr) 3340, 1690.

(VII) D-2-bromo-6-methyl-8beta-(azetidinylcarbonyloxymethyl)-ergoline, m.p. 220°–221° C. (EtOAc); $[\alpha]_D^{20} - 76.8$ (c=0.5 $C_5H_5N$); M+ 419-417.

For $C_{20}H_{24}N_3O_2Br$ (418.35): calc. %C 57.42; H, 5.78; N, 10.05; found %C, 57.32; H, 5.65; N, 9.94; u.v. (MeOH) $\lambda_{max}$276 (9440), 225 (32.280), I.R. (KBr) 3500, 1670.

(IX) D-2-bromo-6-methyl-8beta-(pyrrolydylcarbonyloxymethyl)-9,10-didehydro-ergoline; maleate m.p. 218°–221° C. (EtOH) $[\alpha]_D^{20} + 67$ (c=0.5 MeOH); M+ 432-429.

For $C_{25}H_{28}N_3O_6Br$ (546.4): calc. %C, 54.95; H, 5.17; N, 7.69; found %C, 54.77; H, 5.35; N, 7.39; u.v. (MeOH) $\lambda_{max}$303 (8180), 240 (18.100), 217 (25.780), I.R. (KBr) 1690.

(X) D-2-bromo-6-methyl-8beta-(pyrrolydycarbonyloxy-methyl)-ergoline maleate, m.p. 231°–233° C. (EtOH) $[\alpha]_D^{20} - 49$ (c=0.5 MeOH); M+ 433-431.

For $C_{25}H_{30}N_3O_6Br$ (548.8); calc. %C, 54.75; H, 5.51; N, 7.66; found %C, 54.91; H, 5.74; N, 7.52; u.v. (MeOH) $\lambda_{max}$258 (10.080), 224 (39.600), I.R. (KBr) 1690.

(XI) D-2-bromo-6-methyl-8beta-(piperidinocarbonyloxymethyl)-9,10-didehydroergoline, maleate m.p. 227°–8° C. (EtOH); $[\alpha]_D^{20} + 65.7$ (c=0.5 MeOH); M+ 445-443.

For $C_{26}H_{30}N_3O_6Br$ (566.46); calc. %C, 55.72; H, 5.40; N, 7.50; found %C, 55.51; H, 5.49; N, 7.20; u.v. (MeOH) $\lambda_{max}$302 (10.460), 214 (33.010), I.R. (KBr) 1685.

(XII) D-2-bromo-6-methyl-8beta-(piperidinocarbonyloxymethyl)-ergoline, maleate, m.p. 224°–226° C. (EtOH): $[\alpha]_D^{20} - 40$ (c=0.5 MeOH); M+ 447-445.

For $C_{26}H_{32}N_3O_6Br$ (568.48); calc. %C, 55.52; H, 5.73; N, 7.47; found %C, 55.66; H, 5.83; N, 7.26; u.v. (MeOH) $\lambda_{max}$281 (7330), 224 (29.630), I.R. (KBr) 1685.

(XIII) D-2-bromo-6-methyl-8beta-(perhydroazepinylcarbonyl-oxymethyl)-9,10-didehydroergoline, m.p. 195°–196° C. tartrate (EtOH); $[\alpha]_D^{20} + +52.38$ (c=0.5 $C_5H_5N$); M+ 457-459.

For $C_{27}H_{34}N_3O_8Br$ (608.48); calc. %C, 53.3; H, 5.63; N, 6.91; found %C, 53.21; H, 5.92; N, 6.95; u.v. (MeOH) $\lambda_{max}$302 ($\epsilon$ 112.30), 242 ($\epsilon$ 23750), 228 ($\epsilon$ 22500), 210 ($\epsilon$ 19850), I.R. 1760, 1670, 1595 cm$^{-1}$.

(XIV) D-2-bromo-1,6-dimethyl-8beta-(perhydroazepinyl-carbonyloxymethyl)-ergoline, m.p. 181°–3° C. (maleate) (EtOH 99); $[\alpha]_D^{20} = = -46.2$ (c=0.5, $C_5H_5N$); M+ 475,473.

For $C_{28}H_{36}N_3O_6Br$ (490.52); calc. %C, 56.95; H, 6.14; N, 7.12; found %C, 57.49; H, 6.23; N, 6.99; u.v. (MeOH) $\lambda_{max}$285 m$\mu$ ($\epsilon$ 12.160), 227 m$\mu$ ($\epsilon$ 29.300), I.R. (KBr) 1690 cm$^{-1}$.

(XV) D-2-iodo-6-methyl-8beta-(perhydroazepinylcarbonyl-oxymethyl) ergoline, m.p. 173°–175° C. (ethyl acetate); $[\alpha]_D^{20} = 77.3$ (c=0.5 $C_5H_5N$); M+ 507.

For $C_{23}H_{30}N_3O_2J$ (507.43): calc. %C, 54.44; H, 5.96; N, 8.28; found %C, 54.61; H, 6.04; N, 8.01; u.v. (MeOH) $\lambda_{max}$277 ($\epsilon$ 10.500); 229 ($\epsilon$ 34.400); I.R. (KBr) 1665 cm$^{-1}$.

(XVI) D-2-bromo-6-methyl-8beta-(morpholinocarbonyloxymethyl)-ergoline, maleate, m.p. 213°–216° C. (EtOH); $[\alpha]_D^{20} - 54$ (c=0.5 MeOH); M+ 449-447.

For $C_{25}H_{30}N_3O_7Br$ (564.45): calc. %C, 53.20; H, 5.36; N, 7.45; found %C, 53.13; H, 5.65; N, 7.29; u.v. (MeOH) $\lambda_{max}$289 (9.300), 278 (9.400), 224 (35.820), I.R. (KBr) 1695.

(XVII) D-2-bromo-1,6-dimethyl-8beta-(morpholinocarbonyl-oxymethyl)-ergoline, m.p. 177°–179° C. (EtOAc); $[\alpha]_D^{20} - 92$ (c=0.5 $C_5H_5N$); M+ 463,461.

For $C_{22}H_{28}N_3O_3Br$ (462.4): calc. %C, 57.15; H, 6.10; N, 9.09; found %C, 56.84; H, 6.03; N, 8.93; u.v. (MeOH) $\lambda_{max}$286 (7.900), 228 (27.400), I.R. CHCl$_3$) 1685.

(XVIII) D-2-bromo-6-methyl-8beta-(4,methyl-piperazinyl-carbonyloxymethyl)-ergoline, bitartrate m.p. 208°–210° C. (EtOH); $[\alpha]_D^{20} - 38$, 1 (c=0.5 $C_5H_5N$); M+ 462-460.

For $C_{30}H_{41}N_4O_{14}Br$ (761.6); calc. %C, 47.31; H, 5.43; N, 7.36; u.v. (MeOH) $\lambda_{max}$282 (13200), 226 (22800), I.R. (KBr) 1695.

(XX) D-2-bromo-6-methyl-8beta-(3-azabicyclo [3, 2, 2]-nonanylcarbonyloxymethyl)-ergoline, m.p. 226°–227° C. (MeOH); $[\alpha]_D^{20} - 84.2$ (c=0.5, $C_5H_5N$); M+ 487-485.

For $C_{25}H_{32}N_3O_2Br$ (486.5): calc. %C, 61.73; H, 6.63; N, 8.64; found %C, 61.70; H, 6.85; N, 8.39; u.v. (MeOH) $\lambda_{max}$280 ($\epsilon$ 9680), 227 ($\epsilon$ 34240), I.R. (CHCl$_3$) 1670, 1605 cm$^{-1}$.

(XXI) D-2-bromo-6-methyl-8beta-(2-phenylisopropyl-carbamoyl-oxymethyl)-9,10-didehydroergoline, m.p. 120°–130° C. tartrate (EtOH/ethyl ether); M+ 493, 495.

For $C_{30}H_{34}N_3O_8Br$ (644.5): calc. %C, 55.91; H, 5.32; N, 6.52; found %C, 57.10; H, 5.68; N, 6.52; u.v. (MeOH) $\lambda_{max}$302 ($\epsilon$ 11020), I.R. (KBr) 1600, 1700 cm$^{-1}$.

The novel compounds can be used as drugs in the form in which they are obtained or in the form of suitable salts with mineral or organic acids of the pharmaceutically acceptable types. To this end, they can be suitably formulated in appropriate pharmaceutical compositions in the form of tablets or dragées or drops or capsules, or as a solution or suspension in capsules of soft gelatin for oral use, ampoules for parenteral use, suppositories for enteral use.

It is also possible to prepare delayed release preparations, so as to ensure a therapeutical effect which is prolonged in time.

For all these preparations the fillers and the methods as commonly used in the pharmaceutical practice can be employed.

It has been found that the novel compounds, as obtained according to the present invention show interesting pharmacological properties at very low dosages on several regions and organs of several animal species.

More particularly the novel compounds display a vasodilatory activity on the peripheral circulatory system, an hypotensive activity and a spasmolytic effect on the gastrointestinal smooth muscles or a blocking activity towards the alpha-adrenergic receptors, both in "vitro" and in "vivo".

In the following Table 2 some pharmacological data are reported relating to the above mentioned features, together with the corresponding data for two known compounds used for comparison.

TABLE 2

| Ex. No. | Antiadrenalic activity (a) vitro $EC_{50}$ng/ml | (b) vivo $ED_{50}$ μg/kg. e.v. | AntiBaCl$_2$ (c) vitro $EC_{50}$ μg/ml | activity $DL_{50}$ e.v. in the mouse mg/kg |
|---|---|---|---|---|
| 4 | 10 | 11.2 | 10 | 7.1 |
| 6 | 4.7 | 80.3 | 3.8 | 13.7 |
| 7 | 5 | 50 | 1.4 | 8.7 |
| 10 | 2 | 15.5 | 4 | 15 |
| 12 | 3.7 | 20.2 | 3.5 | 50 |
| 2 | 0.0017 | 8 | 3.1 | 39.4 |
| 16 | 5.8 | 41.9 | 7.5 | 20.5 |
| 18 | 50 | greater than 320 | greater than 100 | 27.3 |
| 20 | 375 | 198 | greater than 100 | 50 |
| nicergoline | (d) 7 | (e) 20 | 2.1 | 74.3 |
| dihydroergotoxine | (e) 78 | (e) 50 | | |

(a) J. Brugger, Helv. Physiol. Pharmacol. Acta 3, 117 (1945)
(b) F.P. Luduena et al. Arch.Int. Pharmacodyn. 122, 111 (1959)
(c) Magnus, Pflügers Arch.Ges.Physiol. 102, 123 (1904)
(d) G. Arcari et al, Brit. J. Pharmacol. 34, 700 P (1968)
(e) G. Arcari et al, Experentia 28, 819 (1972)

More particularly the compound II, described in the Examples, shows some of the above-mentioned activities in selective manner, so as to be particularly useful for the therapeutical use. The product is antagonizing the spasmogenic effect of the adrenaline on the seminal vesicle of guinea pig at concentrations of between 0.1 and 10 pg/ml, as well as the vaso- constricting effect of the noradrenaline on the isolated and perfused caudal arteria of rat, at dosages of between 1 and 10 μg total. Furthermore it antagonizes the contracturing effect of adrenaline and noradrenaline on the "vas deferens" of guinea pig and rat, at concentrations of 0.1 to 10 ng/ml.

The substance antagonizes the spasmogenic action of the barium chloride on the isolated ileum of guinea pig at dosages of between 1 and 5 μg/ml. Such an activity is of the same order as that of nicergoline, but higher than that of the papaverine. On the isolated caudal arteria of rat, the compound II inhibits the vaso-constricting effect as caused by the perfusion with hyperpotassium Ringer's solution. This activity is displayed at the same doses of the nicergoline and of the papaverine (10–100 μg total), but is longer lasting.

In "vivo" the compound II is capable of protecting rats ($ED_{50}$8 μg/kg e.v. and 370 μg/kg per os) and mice ($ED_{50}$51 μg/kg e.v. and 0.61 mg/kg per os), from the lethal effect of the adrenaline. In this test the product shows in the rat an activity 2.5 times higher than that of the nicergoline, when the administration takes place intravenously, whereas its activity is 24 times higher when the administration takes place orally. In the anaesthetized dog the compound, when administered intravenously at dosages of 10–50 μg/kg, does not vary the hearth rate and the myocardial contractility, whereas the arterial pressure and the femoral arterial resistance are reduced, the femoral arterial flow rate being increased by 20 to 100%.

In the anaesthetized cat and rat, the compound causes the arterial pressure to be reduced, starting from dosages of 50 and 30 μg/kg e.v. respectively. In the "pithed" rat the compound, when intravenously administered, antagonizes the hypertensive effect of the adrenaline (ED-50 46 mg/kg).

The extremely selective action of the compound is demonstrated by the fact that the anti-acetylcholinic, anti-histaminic and anti-serotoninic activity, in "vitro", is displayed at concentrations 4500, 800 and 200 times respectively higher than those showing the alpha-blocking effect. Moreover the compound does not antagonize the beta-adrenergic receptors both in the isolated atrium and in the isolated trachea of guinea pig. The $LD_{50}$ for rats and mice is respectively 27.7 mg/kg by intravenous route, and between 0.750 g/kg and 0.45 g/kg per os.

The administration of the substance to Beagle dogs, for a period of 7 months at the dose of about 8 mg/kg per oral route, did not cause modifications of the weight, hematological and hematochemical parameters, and did not cause macroscopic or microscopic alterations of the main organs.

The compound belongs to the class of the ergolene derivatives in which substances are found which cause stimulating effects on the central nervous system (CNS); several behaviour tests have been carried out on animals, in order to assess a possible exciting and hallucinogen action. In the tests carried out (swimming of the rat, reserpine induced ptosis, catatonia induced by tetrabenazine, motility and exploration behaviour of mice and rats modification of the behaviour in the rabbit and in the dog), no evidence were found of any exciting property of the compound; on the contrary, ECG modifications of sedative type were always detected.

The compound II, on the basis of pharmacological and toxicological properties and of the high therapeutical index, can be used as cerebral and peripheral vasodilator, as a antihypertensive and for the cerebral arteriosclerosis.

According to the indications given by the pharmacological tests as above summarily referred to, the foreseen therapeutical use for the compounds of the present invention would be based on a maximum daily dosage of 5 to 30 mg and, as a consequence, on the use of pharmaceutical compositions in which the dosage of the active ingredient is of 1 to 10 mg for the tablets and 1 to 5 mg for the ampoules (taking of course into account the absorption differences above referred to).

Further aspects of the present invention are connected, in addition to those mentioned hereinabove, with particular applications of a few compounds according to this invention in the therapeutics.

More detailedly, are encompassed within the scope of the present invention:

(a) the pharmaceutical compositions for the treatment of disorders of psychogenetic origin, which contain, as the active ingredient, D-2-bromo-1,6-dimethyl-8-beta-(perhydroazepinylcarnbonyloxymethyl) ergoline and its nontoxic pharmaceutically acceptable salts with organic and inorganic acids.

(b) the pharmaceutical compositions for the treatment of asthma, which contain, as the active ingredient, D-2-bromo-6-methyl-8-beta-(morpholino carbonyloxymethyl)-ergoline or its nontoxic pharmaceutically acceptable salts with organic and inorganic acids.

Such aspects of the present invention will become clearer from the ensuing description of same.

It has been found, in fact, that the compound described as D-2-bromo-1,6-dimethyl-8beta-(perhydroazepinylcarbonyloxymethyl) ergoline, corresponding to the formula (3) hereof, is endowed with particular

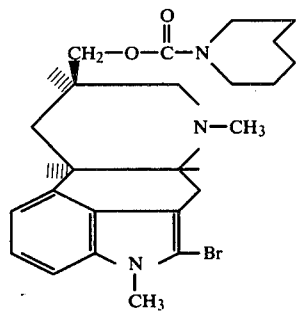

pharmacological properties which render it usable from the therapeutical standpoint as an antidepressant agent.

The compound described by the formula (3) has the empirical formula $C_{24}H_{32}N_3O_2Br$, mol. wt. 474.5. It gives salts with both mineral and organic acids of nontoxic type and acceptable for therapeutical use. These salts are water-soluble and are soluble in the physiological solutions: e.g. the maleate (II) ($C_{28}H_{36}N_3O_6br$; m.p. 181° C.-183° C.) or the methanesulfonate ($C_{25}H_{36}N_3O_5Br$ S; mol. wt. 570.58; m.p. 225° C.-231° C.), and can be prepared, according to conventional methods, by treating the compound (3) with the equivalent amount of acid in an aqueous medium or in an appropriate solvent or mixtures of organic solvents such as alcohols, ethers, lower aliphatic ketones and others, taken individually or in appropriate mixtures as will be specified in the ensuing Examples.

The pharmacological activity of the compound of formula (3) is displayed in a set of appropriate assays, carried out in the experiment animals and is especially cons-picuous and significant in the following test runs:

| | | | |
|---|---|---|---|
| Antagonism to ptosis from reserpine B.. M. ASKEW Life Sciences, 2,725,1963 | Compd. (3) | $ED_{100}$ | 0.01 mg/kg,orally |
| | imipramine | $ED_{100}$ | 25 mg/kg,orally |
| Anorexia | Cpd. (3) | $ED_{100}$ | 5 mg/kg,orally |
| | amphetamine | $ED_{100}$ | 5 mg/kg,orally |
| Anti-Parkinson activity | Cpd. (3) | $ED_{100}$ | 20 mg/kg,orally |
| | L-dopa | $ED_{100}$ | 300 mg/kg,orally |
| Toxicity | $LD_{50}$ mice, orally | | 600 mg/kg |
| | $LD_{50}$ mice, intravenously | | 65–83 mg/kg |

The comparative examination with comparison substances which are universally known for their properties has made conspicuous significantly more powerful actions for the compound (3), for example in the form of its maleate, as can be seen from the data reported hereinabove.

The examination of the acute toxicity, moreover, shows that the compound is well tolerated and poorly toxic so that a favorable therapeutical index is the result.

If the power of the action exhibited by the novel compound as compared with ipramine is duly considered, the advantage which has been achieved becomes conspicuous, and the technical advance as well.

For the novel compound to be used in the therapeutics, it can be formulated in the form of an appropriate salt, consistently with the indications which have been given in the foregoing, into a number of pharmaceutical compositions for oral use, for parentheral use and also for rectal use. Such compositions can take the form of tablets or dragees or solutions, drops, or soft gelatine capsules, of hard gelatine capsules for the administration by the oral route. For such a use, the compound of the formula (3) can also be formulated in the delayed-release form. The pharmaceutical compositions for the parenteral administration, in their turn, comprise ampoules containing a solution which is adapted for the intramuscular or the intravenous administration, or for transcutaneous administration, as prepared with physiological solution or with appropriate nonaqueous solvents. Lastly, the pharmaceutical compositions for rectal route administration are the suppositories.

The excipients, dispersants, lubricants, the auxiliary substances, the solvents for such preparations are those which are known to the skilled chemist and are adapted to afford a satisfactory biological availability of the active principle and, at any rate, this will be specifically mentioned in the Examples.

The pharmaceutical forms which have been mentioned contain unit dosages of active principle, comprised between 0.1 mg and 25 mg per dosage unit. The active principle is intended as being administered as such or preferably in the form of one of its salts. Especially suitable have proven to be the maleate and the methanesulfonate which lend themselves quite fairly by virtue of their stability characteristics.

The pharmaceutical compositions cited above are adapted for the treatment of disorders of psychogenetic origin and especially in those classified under the psychotic disorders, autonomous and visceral psychophysiological disorders, psychoneurotic disorders, personally disorders and all those ailments in which the therapy with antidepressant agents is indicated.

The ensuing Examples are merely illustrative of the present invention without limiting the scope thereof in any wise.

EXAMPLE 22

D-2-bromo-1,6-dimethyl-8beta-(perhydroazepinyl-carbonyloxymethyl) ergoline maleate.

1 gram of D-2-bromo-1,6-dimethyl-8beta-(perhydroazepinylcarbonyloxymethyl-ergoline, dissolved in 10 mls of abs. EtOH (boiling) are supplemented with 0.250 g of maleic acid dissolved in 3 mls of the same solvent. Upon cooling, the salt crystallizes and is collected on a filter and crystallized from 35 mls of abs. EtOH, and 0.9 g of pure maleate are thus obtained.

m.p. 181° C.-183° C.: $[\alpha]_D^{20} = 46.2$ (c=$2C_5H_5N$); M+ 475/473:

Elemental analysis for $C_{28}H_{36}N_3O_6Br$

|  | C% | H% | N% |
|---|---|---|---|
| Calcd. | 56.95 | 6.14 | 7.12 |
| found | 57.49 | 6.23 | 6.99 |

UV analysis: $\lambda_{max}^{MeOH}$ 285 m$\mu$ ($\epsilon$ 12,160) 227 m$\mu$ ($\epsilon$ 29,300)

IR (KBr) 1690 cm$^{-1}$

EXAMPLE 23

D-2-bromo-1,6-dimethyl-8beta-(perhydroazepinylcarbonyloxymethyl) ergoline methanesulfonate 1 g of D-2-bromo-1,6-dimethyl-8beta-(perhydroazepinylcarbonyloxy methyl) ergoline dissolved in 25 mls of boiling acetone are treated with 0.15 mls of methanesulfonic acid. The salt immediately precipitates and is collected on a filter and crystallized from acetone-methanol (3:1), 1 g of pure methanesulfonate being thus obtained.

m.p. 225° C.-231° C.: $[\alpha]_D^{20} = -55$ (c=0.5 C$_5$H$_5$N) M+ 475.473

Elemental analysis for:

| C$_{25}$H$_{36}$N$_3$O$_5$Br S | C% | H% | N% |
|---|---|---|---|
| CALCD. | 52.63 | 6.36 | 7.37 |
| found | 52.8 | 6.12 | 7.23 |

UV $\lambda_{max}^{MeOH}$ 286 m$\mu$ ($\epsilon$ 10.030) 228 m$\mu$ ($\epsilon$ 35.000) 208 m$\mu$ ($\epsilon$ 23.650)

EXAMPLE 24

Preparation of tablets.

0.5 g of D-2-bromo-1,6-dimethyl-8beta-(perhydroazepinylcarbonyloxymethyl) ergoline maleate are admixed with 550 g of lactose and 291.5 g of starch and wetted with an alcoholic solution of 8 g of gelatine and then screened. After drying there are added 60 g of starch, 60 g of talc, 10 g of magnesium stearate and 20 g of dispersed silica.

The mixture is blended carefully and then compressed into 5,000 200-mg tablets, each containing 1 mg of the active principle.

EXAMPLE 25

Preparation of injectable ampoules.

1 g of D-2-bromo-1,6-dimethyl-8beta-(perhydroazepinylcarbonyloxymethyl) ergoline pethanesulfonate are dissolved in 500 mls of pyrogen-free distilled water, whereafter there are added 10 mls of 95% ethyl alcohol and 20 mls of propylene glycol. After making up to 2,000 mls with dist. water, filtration under sterile conditions is effected and 1,000 ampoules are filled under a nitrogen atmosphere. There are obtained in this manner 2-ml ampoules each of which contains 0.5 mg of the active principle.

EXAMPLE 26

Preparation of suppositories.

2.5 g of D-2-bromo-1,6-dimethyl-8beta-(perhydroazepinylcarbonyloxymethyl) ergoline are slurried in 25 mls water, the slurry is dispersed into 25 g of lanolin. The mixture is introduced in a base mass for suppositories, made with 937.5 g of cocoa butter and 10 g of white beeswax, the whole being kept melted on a water bath. The molten mass is cast in 1-g suppository molds.

Coming now to examining the anti-asthmatic pharmaceutical compositions it has been ascertained that the compound described as D-2-bromo-6-methyl-8beta-(morpholinocarbolynoxymethyl)-ergoline, corresponding to the formula (4) is endowed with quite special

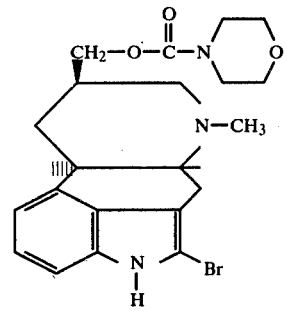

which render it particularly recommendable for the therapy of asthma. The compound of the formula (4) has the empirical formula C$_{21}$H$_{26}$N$_3$O$_3$Br and a mol. wt. of 448.38. It gives, with mineral and organic acid of nontoxic and pharmacologically acceptable nature, a number of salt. These are soluble in water as well as in the physiological solutions. Such are for example the maleate C$_{25}$H$_{30}$N$_3$O$_7$Br, m.p. 213° C.-216° C., or the methanesulfonate C$_{22}$H$_{30}$N$_3$O$_6$BrS, m.p. 265° C.-266° C. and can be prepared according to the conventional methods by treating the compound (4) with the equivalent quantities of the acid in an aqueous medium or in appropriate organic solvents and their mixtures such as the alcohols, the ethers, the lower aliphatic ketones and others, taken individually or in appropriate mixtures with each other as will be detailed in the Examples hereinafter. The pharmacological activity of the compound of formula (4) is unfolded in appropriate assays, carried out on the test animals and is especially conspicuous in the following test runs:

| Anti-asthmatic activity | Compound (4) | ED$_{100}$ 0.25 mg/kg orally |
|---|---|---|
| Goose, Immunology, 16, 749, 1969 | Sodium chromoglycate | ED$_{100}$ 5 mg/kg intrav. |
| Antidepressant activity | Compound (4) imipramine | ED$_{100}$ 5 mg/kg orally ED$_{100}$ 25 mg/kg |
| Myorelaxing activity | Compound (4) phenobarbital | ED$_{100}$ 100 mg/kg ED$_{100}$ 100 mg/kg |
| Toxicity | LD$_{50}$ mice orally LD$_{50}$ mice intrav. | 180 mg/kg 18-22 mg/kg |

The comparative examination with comparison substances which are universally known for their pharmacological properties has made it conspicuous that the compound (4) is capable of displaying both selectivity and a powerful activity against asthmatic seizures. The manifold power of the compound (4) is also displayed in that it exerts a powerful adrenergic activity "in vitro", as has been previously shown, along with a considerable antidepressant activity which can be compared to that of imipramine and a remarkable myorelaxing activity which is comparable to that of phenobarbital as has been shown hereinabove. All of these activities of an accessorial nature which unfold themselves at dosages which are considerably higher than those which cause the antiasthmatic effect, should be regarded as favorable factors in the sense that they improve the pharmacological pattern of the product, so that a possible therapeutic use of the product for patients suffering from asthma, as a pain-reliever, can be forecast.

The examination of the toxicity shows a considerable margin of safety of the product, the toxic effects of which become apparent only beyond 1,000 the therapeutic dosage.

The technical advance is then apparent as afforded in the field of the anti-asthmatic medicaments the universally accepted comparison sample for which is sodium chromoglycate: the activity of the latter under the pharmacological aspect is manifested only by the parentheral administration (intravenously), and, in man by inhalation of the dispersed powder.

In the case of the compound (4) the action is manifested not only at considerably lower dosage levels, but also, that which is most significant and important, by the oral route.

For the utilization in the therapeutics, the novel compound can be formulated in the form of an appropriate salt, according to the suggestions reported above, in various pharmaceutical compositions for oral, parentheral or ractal administration. Such compositions can be in the form of tablets, dragees or solutions as such or capsules of soft or hard gelatin for the administration through the oral route. Through the latter route, the compound (4) can be administered as formulated in the delayed-release form. The excipients, dispersants, lubricants, ancilliary substances and the solvents for the pharmaceutical formulations are those which ar known to a skilled chemist and are adapted to achieve a satisfactory biological availability for the active principle.

The compositions adapted to the parentheral administration, in their turn, comprise ampoules which contain a solution suitable for being administered intramuscularly, intravenously or transcutaneously, as prepared with physiological solutions or with appropriate solvents. Finally, the pharmaceutical compositions for rectal administration are suppositories to be formulated with the procedures known to the skilled chemists.

The pharmaceutical forms mentioned above contain dosage units of active principle comprised between 0.1 mg and 25 mg per dosage unit. The active principle is intended as administered as such or preferably in the form of a salt thereof. Especially suitable are the maleate and the methanesulfonate which lends themselves very well by virtue of their physical and chemical stabilities.

The following Examples are merely illustrative and are no limitations to the scope of the present invention.

EXAMPLE 27

D-2-bromo-6-methyl-8beta-(morpholinocarbonyloxymethyl)ergoline maleate. 1 g of D-2-bromo-6-methyl-8beta-(morpholinocarbonyloxymethyl) ergoline in 15 mls of abs. EtOH (boiling) are treated with a solution of 0.240 g of maleic acid in the same solvent. Upon cooling and dilution with ½ volume of ether, the precipitate is collected on a filter and crystallized from 95% EtOH and 1.1 g of pure product is thus obtained.

m.p. 213° C.-216° C.; $[\alpha]_D^{20} = -54°$ (c=0.5 methanol), M+ 449.447.

Elemental analysis for $C_{25}H_{30}N_3O_7Br$:

|  | C% | H% | N% |
| --- | --- | --- | --- |
| Calcd. | 53.20 | 5.36 | 7.45 |
| found | 53.13 | 5.65 | 7.29 |

UV $\lambda_{max}^{MeOH}$ 282 mμ (ε 9300) 278 mμ (ε 9400) 224 mμ (ε 35820)

IR (KBr) 1695 cm$^{-1}$

EXAMPLE 28

D-2-bromo-6-methyl-8beta-(morpholinocarbonyloxymethyl)ergoline methanesulfonate.

1 g of D-2-bromo-6-methyl-8beta-(morpholinocarbonyloxymethyl) ergoline in 30 mls of boiling acetone are treated with 0.236 g of methanesulfonic acid. The salts precipitates immediately and is collected on a filter and crystallized from methanol, 1 g of pure product being thus obtained. m.p. 265° C.-266° C.: $[\alpha]_D^{20} = -54$(c=0.5 $C_5H_5N$)M+449,447,

| Elemental analysis | C% | H% | N% |
| --- | --- | --- | --- |
| Calcd. | 48.53 | 5.55 | 7.72 |
| found | 48.56 | 5.38 | 7.76 |

UV$\lambda_{max}^{MeOH}$ 276 mμ (ε 9350) 226 mμ (ε 34000) 210 mμ (ε 21600)

EXAMPLE 29

Preparation of tablets.

50 g of D-2-bromo-6-methyl-8beta-(morpholinocarbonyloxymethyl) ergoline maleate are admixed with 810 g of cornstarch, 1050 g of microcrystalline cellulose and 85 g of talc. The admixture is introduced in a powder blender and is rotated until an even distribution of the active principle in the excipients is achieved. Subsequently, the powder is directly tabletted in a tabletting machine, in the form of tabloids having a diameter of 2 cm and a weight of 2 grams. The thusly obtained tabloids are fed to a granulator. The granulate is supplemeted by 5 g of magnesium stearate and then subjected to the final tabletting for obtaining 10,000 tablets of the weight of 200 mg, each of which contains 5 mg of the active principle.

EXAMPLE 30

Preparation of ampoules.

2.5 g of D-bromo-6-methyl-8beta-(morpholinocarbonyloxymethyl) ergoline methanesulfonate are dissolved in a mixture of 10 mls of 95% EtOH and 20 ml dist. water exempt from pyrogens. The solution is then diluted with 20 mls of bidist. glycerol and then made up to 2,000 mls with pyrgen free dist. water. Filtration in sterile environment is effected, whereafter the ampoules are filled under a nitrogen blanket to make 1,000 ampoules of the 2 ml size, thus obtaining ampoules each of which contains 2.5 mg of the active principle.

EXAMPLE 31

Preparation of suppositories.

70 g of polyoxyethylenesorbitane monostearate, 40 g of sorbitan stearate, 155 g of paraffin oil, 130 g of stearic alcohol are melted together.

To the molten mass kept at a temperature of from 50° C. to 60° C. there is added a solution of D-2-bromo-6-methyl-8beta-(morpholinocarbonyloxymethyl) ergoline methanesulfonate (5 g dissolved in 600 mls dist. water) kept at a temperature of from 50° C. to 60° C. The mixture is vigorously stirred at 50° C. to emulgate it, whereafter is allowed to cool at room temperature and the molds are filled. There are obtained 1,000 suppositories each of which contains 5 mg of the active principle.

We claim:

1. A carbamate of 2-haloergoline or 2-haloergolene, having the formula:

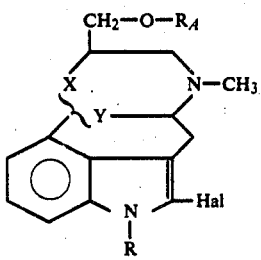

wherein R, $R_A$, x⁀y, Hal are defined as follows:

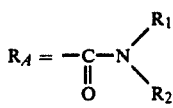 (a)

wherein $R_1$ and $R_2$ independently represent (i) H, $C_1$-$C_8$ straight alkyls, or $C_1$-$C_8$ branched alkyls; $C_3$-$C_{12}$ alicyclic groups; phenyl, benzyl, phenethyl, phenethyl substituted by an alkyl group, a dioxymethylene group, hydroxyl, or halogen; or $R_1$ and $R_2$ are connected to each other in the form:

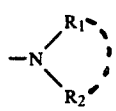

to form (ii) a $C_3$-$C_7$ cyclic or bicyclic ring structure (iii) a heterocyclic ring structure of the formula:

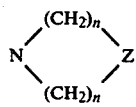

wherein Z represents an oxygen atom or the group N—$R_3$, wherein $R_3$ is H, or alkyl, and n is 2;

(b) R is H, $C_1$-$C_5$ straight alkyl or $C_1$-$C_5$ branched alkyl;

(c) x⁀y represents —$CH_2$—CH< or —CH=C<; and (d) Hal is Cl, Br or I.

2. D-2-bromo-6-methyl-8beta-(N,N-dimethylcarbamoyloxymethyl)-9,10-didehydroergoline, according to the claim 1.

3. D-2-bromo-6-methyl-8beta-(perhydroazepinylcarbonyloxymethyl)-ergoline, according to the claim 1.

4. D-2-chloro-6-methyl-8beta-(perhydroazepinylcarbonyloxymethyl)-ergoline, according to claim 1.

5. D-2-bromo-6-methyl-8beta-(N,N-dimethylcarbamoyloxymethyl)ergoline, according to claim 1.

6. D-2-bromo-6-methyl-8beta-(N,N-diethylcarbamoyloxymethyl)-9,10-didehydroergoline, according to claim 1.

7. D-2-bromo-6-methyl-8beta-(N,N-diethylcarbamoyloxymethyl)-ergoline, according to claim 1.

8. D-2-bromo-6-methyl-8beta-(azetidinylcarbonyloxymethyl)-ergoline, according to claim 1.

9. D-2-bromo-6-methyl-8beta-pyrrolydylcarbonyloxymethyl)-9,10-didehydroergoline, according to claim 1.

10. D-2-bromo-6-methyl-8beta-(pyrrolydylcarbonyloxymethyl)-ergoline, according to claim 1.

11. D-2-bromo-6-methyl-8beta-(piperidinecarbonyloxymethyl)-9,10-didehydroergoline, according to claim 1.

12. D-2-bromo-6-methyl-8beta-(piperidinocarbonyloxymethyl)-ergoline, according to claim 1.

13. D-2-bromo-6-methyl-8beta-(perhydroazepinylcarbonyloxymethyl)-9,10-didehydroergoline, according to claim 1.

14. D-2-bromo-1,6-dimethyl-8beta-(perhydroazepinylcarbonyloxymethyl)-ergoline, according to claim 1.

15. D-2-iodo-6-methyl-8beta-(perhydroazepinylcarbonyloxymethyl)-ergoline, according to claim 1.

16. D-2-bromo-6-methyl-8beta-(morpholinocarbonyloxymethyl)-ergoline, according to claim 1.

17. D-2-bromo-1,6-dimethyl-8beta-(morpholinocarbonyloxymethyl)-ergoline, according to claim 1.

18. D-2-bromo-6-methyl-8beta-(4-methylpiperazinylcarbonyloxymethyl)-ergoline, according to claim 1.

19. D-2-bromo-6-methyl-8beta-(3-azabicyclo[3,2,2-]nonanylcarbonyloxymethyl)-ergoline, according to claim 1.

20. D-2-bromo-6-methyl-8beta-(2-phenylisopropylcarbamoyloxymethyl)-9,10-didehydroergoline, according to claim 1.

21. A carbamate of 2-haloergoline or 2-haloergolene, having the formula:

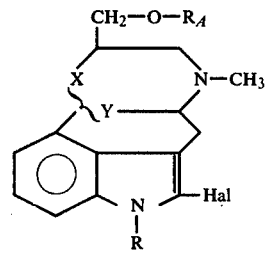

wherein
$R_A$ represents the group:

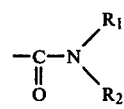

in which $R_1$ and $R_2$ independently represent H, $C_1$-$C_8$ straight alkyl, $C_1$-$C_8$ branched alkyl, phenyl, benzyl, or phenethyl, or $R_1$ and $R_2$ are connected to each other in the form:

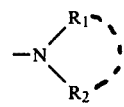

to form a piperidino, hexamethylenimino, azabicyclo [3,2,2-] nonane group:

R is H, $C_1$-$C_5$ straight alkyl, or $C_1$-$C_5$ branched alkyl;
x⁀y represents —$CH_2$—CH< in both the possible stereoisomeric configurations, or —CH=C<; and Hal is chlorine, bromine or iodine.

22. A pharmaceutical composition for use as cerebral and peripheral vaso-dilator, as anti-hypertensive and in the therapy of cerebral arteriosclerosis, containing as the active ingredient a compound according to claim 1 and a pharmaceutically acceptable carrier therefor.

23. A pharmaceutical composition for the treatment of disorders of psychogenetic nature, containing, as the active ingredient, D-2-bromo-1,6-dimethyl-8beta-(perhydroazepinylcarbonyloxymethyl)-ergoline or a nontoxic pharmcologically acceptable salt thereof with an inorganic or organic acid along with an appropriate pharmacologically acceptable pharmaceutical carrier.

24. A pharmaceutical composition according to claim 23, wherein said compound is present in an amount comprised between 0.1 mg and 25 mg per dosage unit.

25. Pharmaceutical compositions for the treatment of asthma, containing, as the active ingredient, D-2-bromo-6-methyl-8beta-(morpholinocarbonyloxymethyl)-ergoline or a nontoxic pharmacologically acceptable salt thereof with an organic or inorganic acid, along with an appropriate pharmaceutically acceptable pharmaceutical carrier.

* * * * *